United States Patent [19]

Sugiyama et al.

[11] Patent Number: 4,952,322
[45] Date of Patent: Aug. 28, 1990

[54] METHOD FOR ABSORBING FREE HEMOGLOBIN FROM BLOOD

[75] Inventors: Masafumi Sugiyama, Kako; Yoshiko Nagatsuma, Hiroshima, both of Japan

[73] Assignee: Japan Medical Supply Co., Ltd., Hiroshima, Japan

[21] Appl. No.: 278,667

[22] Filed: Dec. 1, 1988

[30] Foreign Application Priority Data

Dec. 7, 1987 [JP] Japan ................................ 62-308905

[51] Int. Cl.$^5$ ............................................. B01D 15/00
[52] U.S. Cl. ...................................... 210/679; 210/691
[58] Field of Search ................................ 210/679, 691

[56] References Cited

U.S. PATENT DOCUMENTS 4,814,077 3/1989 Furuyoshi et al. .................. 210/679

FOREIGN PATENT DOCUMENTS 55-4417 1/1980 Japan .
56-51780 12/1981 Japan .

Primary Examiner—Ivars Cintins
Attorney, Agent, or Firm—Kramer, Brufsky & Cifelli

[57] ABSTRACT

An absorbent for absorbing free hemoglobin from blood is provided, which comprises a water insoluble porous carrier having phenyl and/or phenol groups on the surface of the carrier. The phenyl and/or phenol groups may be a constituent of the carrier itself, or they may be a constituent of a separate compound affixed to the carrier surface, directly or through use of a coupling agent. Also provided is a method for absorbing free hemoglobin from whole blood or separated plasma which includes contacting the whole blood or plasma with the absorbent.

6 Claims, 1 Drawing Sheet

METHOD FOR ABSORBING FREE HEMOGLOBIN FROM BLOOD

FIELD OF THE INVENTION

This invention relates to absorbents which selectively absorb free hemoglobin. More particularly, this invention relates to absorbents which extract, by absorbing, free hemoglobin from blood plasma, and thereby prevent free hemoglobin from causing deleterious effects on the human body.

BACKGROUND OF THE INVENTION

It is well known that medical treatments which use extracorporeal blood circulation devices such as artificial kidneys and pump-oxygenators often cause hemolysis, i.e., the liberation of hemoglobin from red blood cells. Free hemoglobin in the blood resulting from hemolysis may cause various kinds of complications in the human body. Although free hemoglobin will normally bind with haptoglobins, a group of glyproteins in serum, to form complexes which will eventually be disposed of in the reticuloendothelial system, the extent of hemolysis is often greater than the capability of disposition thereof. When there is more free hemoglobin in the blood than can be disposed of, the free hemoglobin acts as a histotoxic substance which can ultimately cause a renal insufficiency.

Similarly, hemolytic anemia, which is a type of autoimmune disease, may also cause a large volume of free hemoglobin to be liberated into blood plasma and lead to various kinds of complications.

It is believed that medical complications associated with free hemoglobin can be prevented by removing free hemoblobin from the blood. In the past, semi-permeable membranes have been used to separate and remove free hemoglobin from other blood components. Efforts to remove free hemoglobin from blood have also been made using absorbent materials which will selectively absorb the free hemoglobin.

Activated charcoal is a material that has been practically used as an absorbent for hematocatharsis, however, the material has little or no affinity for hemoglobin and therefore has not been used for this purpose.

Absorbents for free hemoglobin which are presently known are based upon natural haptoglobin. Heretofore, haptolglobin has been bound to insoluble carriers in an effort to take advantage of haptoglobin's natural affinity for selectively binding free hemoglobin. This type of absorbent is disclosed for example, in Japanese Patent Publications, Nos. 55-4417 and 56-51780.

The haptoglobin-based absorbents have not proved to be satisfactory for a number of reasons. In order to obtain an effective absorbent, it is necessary that the haptoglobin retain its activity after it has been affixed to an insoluble carrier. However, it has proven to be extremely difficult to isolate the haptoglobin from separated, refined blood plasma and affix the naturally occurring glycoprotein to the surface of a carrier without rendering the substance inactive. In fact, no practical method has yet been found. Even in those instances where active haptoglobin has successfully been affixed to the carrier, the passage of time often leads to a decrease in activity of the absorbent. As result, the method of absorbing free hemoglobin with haptoglobin-based carriers has not met with a great deal of success.

Another disadvantage of the haptoglobin-based absorbents is that they are deactivated upon sterilization. Pre-sterilization, however, is particularly important for medical uses.

Accordingly, it is one primary objective of the present invention to provide absorbents which selectively absorb free hemoglobin and which are easily produced.

Another objective of this invention is to provide absorbents for free hemoglobin which remain effective upon sterilzation.

These and other objectives of the present invention will become apparent from the specification.

SUMMARY OF THE INVENTION

This invention provides an absorbent for selectively absorbing free hemoglobin, which comprises a water insoluble porous substance having phenyl and/or phenol groups on its surface, and also provides a method for making the absorbent. There is also provided a blood treatment system for removing free hemoglobin in blood to prevent deleterious conditions associated therewith by employing the absorbents of the present invention.

The absorbents of the present invention can be filled into a column or other similar apparatus through which a free hemoglobin-containing solution, such as blood, is to be passed. As the solution is passed through the column, the free hemoglobin is selectively absorbed and extracted. It is believed that the selective absorption is due to some form of reaction between the free hemoglobin and the phenyl and/or phenol groups on the surface of the porous carrier.

DETAILED DESCRIPTION OF THE INVENTION

Figure 1:
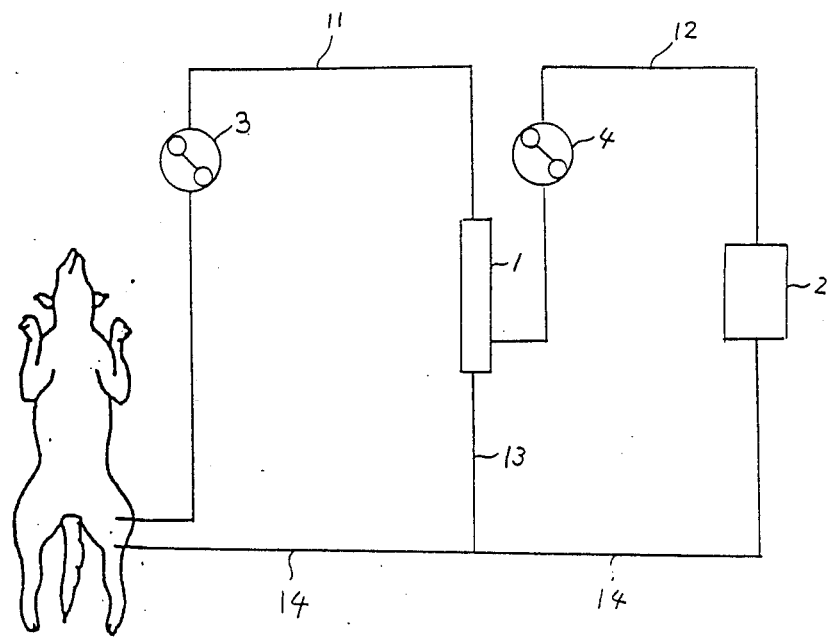
FIG. 1 is a schematic representing one typical example of an extracorporeal circulation system for extracting free hemoglobin in blood by using an absorbent of the present invention.

The absorbent of the present invention comprises a porous substance or "carrier" having phenyl and/or phenol groups on the carrier surface.

The water insoluble porous substance or carrier can be a material such as porous glass, porous silica, porous alumina, cellulose gel, agarose gel, dextran gel, polyacrylamide gel, vinyl polymer gel, oxirane acrylic beads and the like. Particularly preferred materials are porous glass and porous silica. Porous substances having average pore sizes ranging from about 60 A to about 500 A are desirable, since the modified substance will then have excellent absorbability for free hemoglobin while absorbing only a small portion of the blood proteins.

The composition to be attached to the surface of the water insoluble porous carrier is a low molecular weight compound containing at least one phenyl or phenol group. The phenyl group referred to in the invention is symbolized by the chemical formula

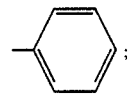

the phenol group is symbolized by the chemical formula

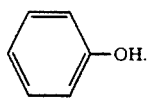

Examples of phenyl and/or phenol containing compositions to be attached to the surface of the carrier include tyramine, tyrosine, phenylalanine, aminophenol, adrenalin, octopamine, noradrenalin, hydroxytyramine, hydroxytryptamine, bufotenine, dihydroxyphenylalanine, phenylglycine, phenylenediamine, acetamidophenol, allylphenol, aminonitrophenol, 2-aminophenol-4-sulfonic acid, anilinophenol, azodiphenol, 4-bromo-2-nitrophenol, bromophenol, 2-chloro-4-nitrophenol, chlorophenol, diaminophenol, dibromonitrophenol, dibromophenol, dichloro-4-nitrophenol, dichlorophenol, 2,6dimethoxyphenol, dinitrophenol, hydroxybenzaldehyde, hydroxybenzoic acid, hydroxybenzophenone, hydroxybenzyl alcohol, 3-hydroxy-4-methoxybenzaldehyde, 3-hydroxy-4methoxybenzoic acid, 4-hydroxy-3-methoxybenzyl alcohol, 4-hydroxy-3-nitrobenzenesulfonic acid, hydroxyphenylacetic acid, 3-hydroxy-3-phenylpropionic acid, 3-hydroxyphenylpropionic acid, hydroxyphthalic acid, hydroxystyrene and 2-hydroxyterephthalic acid. The preferred phenyl and/or phenol containing compositions are tyramine, tyrosine, phenylalanine, aminophenol or some combination thereof. Tyramine is particularly preferred.

The phenyl and/or phenol containing composition can be affixed to the surface of the porous carrier by one of a number of known methods. One method is to chemically affix the low molecular weight composition containing phenyl and/or phenol groups to the surface of the water insoluble porous carrier. Another method is to coat the phenyl and/or phenol containing composition on the surface of the water insoluble porous carrier. Still another method is to preform a carrier with a composition containing phenyl or phenolic side chains. Of of the three forementioned methods, the first mentioned is the most preferable.

Methods which are publicly known in the area of fixed enzyme and affinity chromatography may be used to fix the low molecular weight compounds having phenyl and/or phenol groups to the water insoluble porous carrier. For example, when reactive groups such as hydroxyl groups, carboxyl groups, epoxy groups and/or amino groups exist on the surface of the porous carrier, such reactive groups may be utilized as a binder to chemically bind the porous carrier directly to a composition having phenyl and/or phenol groups. For example, oxirane acrylic beads (EUPERGIT®C) contain epoxy groups at their surface, which can directly react with amino group containing compositions such as tyramine, tyrosine and aminophenol. Alternatively, it is within the scope of the present invention that the carrier and phenyl and/or phenol containing composition be bound indirectly by utilizing a carrier which is reactively bound with other compounds containing such reactive groups, and then reacting the composition having phenyl and/or phenol groups with the modified carrier.

When the porous carrier has silanol groups on its surface, as for example when such carrier is formed from glass or silica or the like, the silanol groups can be reacted with a silane coupling agent. The silane coupling agent on the surface of the carrier is then available for reaction with the composition having phenyl and/or phenol groups. γ-glycydoxypropyltrimethoxysilane, γ-glycydoxypropylmethyldiethoxysilane, N-β-aminoethyl- γ-aminopropylmethyldimethoxysilane, γ-aminopropyltriethoxysilane,γ-mercaptopropyltrimethoxysilane, and vinyltrichlorosilane are examples of the silane coupling agents which can be used in preparing the absorbents of the present invention. Of these named silane coupling agents, dialkoxysilane compounds such as γ-glycydoxypropyl methyldiethoxysilane, and N-B-aminoethyl- γ-aminopropylmethyldimethoxysilane are particularly preferred.

Porous glass and porous silica contain a constituent which can be eluated in hot water and which should be extracted by washing before using the absorbent prepared therewith. The precise nature of the constituent eluated from porous glass or porous silica is not known. However, it is believed that the constituent is a water soluble silica compound. If the absorbent is to be used for extracorporeal blood circulation, it is possible that the constituent will become dissolved in the blood. The constituent may also be dissolved in the steam sterilization process. In either situation, dissolved material could enter the body, wherein a large amount of the constituent can undesirably activate the blood coagulation system. Use of the dialkoxysilane compounds facilitates the quick extraction of such constituent and therefore the dialkoxysilanes are the preferred silane coupling agents. The Soxhlet's extractor is conveniently used for washing the absorbent to extract the undesirable constituent.

Other methods for binding the composition having phenyl and/or phenol groups to a carrier surface include activating the surface by known methods such as the halogenized cyanogen method, epichlorohydrine method, bisepoxyed method, halogenized triazine method, bromoacetylbromide method, ethylchloroformate method and/or the 1.1'-carbonyldiimidazole method.

The absorbents of the present invention are particularly useful for extracting free hemoglobin from blood by means of extracorporeal circulation. In order to extract free hemoglobin from the blood in this fashion, a column having a blood inlet port and an outlet port is filled with an absorbent of the present invention. Blood is then continuously passed through the filled column. The blood contacted with the absorbent in the column can be whole blood or alternatively, plasma separated from red blood cells in a plasma separator can be contacted with the absorbent. In the latter situation, the post-treatment plasma is remixed with previously separated blood cells and then returned to the body.

FIG. 1 is an example of a typical system useful for this type of method. In the FIGURE, 1 is a plasma separator and 2 is the absorption column. The plasma separator is a device for separating plasma from blood cells by means of a semipermeable membrane or centrifuge. Any type of established device may be used. Whole blood, which is collected from the living body, is introduced into the plasma separator 1 through the tubing 11, wherein the plasma is separated from the blood cells. After the plasma is separated from the blood cells, it is passed through tubing 12, and introduced into the absorption column 2. Absorption column 2 is filled with a porous carrier having phenyl and or phenol groups on its surface in accordance with the present invention. After the free hemoglobin has been absorbed and extracted, the plasma is delivered out through tubing 14.

Simultaneously, blood cells which were separated from the plasma by means of the plasma separator 1, are delivered out through tubing 13 and join to the plasma from tubing 14 for return to the living body.

Where extracorporeal circulation is being performed, the absorbent may be used alone, or it may be used jointly with other extracorporeal blood circulation devices such as artificial kidneys or pump-oxygenators. In the latter cases, placing the absorption column after the artificial kidney or the pump-oxygenator will enhance effectiveness. The absorbent may also be integratedly used with the artificial kidney or the pump-oxygenator.

When used for medical applications, the absorbents of the present invention may be subject to sterilization. Autoclave sterilization and gamma ray sterilization are regarded as the desired sterilization methods.

EXAMPLE 1

Five grams of porous glass beads (Pure Chemicals, Wako FPG-250) with an average pore size of 233A and a specific surface area of 99 $m^2$/gm were dipped into a 0.5% aqueous solution of γ-glycydoxypropyltrimethoxysilane. The preparation was then mixed for two hours to cause the silanol groups on the surface of the porous glass to react with the γ-glycydoxypropyltrimethoxysilane. After the two hours, the porous glass was filtered off and the water wiped from the surface. The porous glass was then dried at a temperature of 120° C. for 3 hours.

1 gm of the dried porous glass was then dipped in 50 ml of a 1% carbonate buffer solution of tyramine (0.1M, pH 9.8) and the preparation was then shaken at a temperature of 60° C. for 20 hours. During this time, the epoxy groups of γ-glycydoxypropyltrimethoxysilane reacted with the amino groups of the tyramine.

Upon completion of the reaction, the porous glass carrier with tyramine was washed with 0.1N sodium hydroxide solution and water to remove the excess tyramine. The porous glass was then treated for two hours in an autoclave at 120° C. in order to open the chain of non-reacted epoxy groups. After treatment in the autoclave, the porous glass was washed with water to finally obtain an absorbent comprising porous glass with phenol containing tyramine fixed on the surface.

0.2 grams of the thus prepared absorbent was then mixed with 4 ml of hemolyzed plasma (concentration of free hemoglobin: 232.7 mg/dl, total protein concentration: 7.0 g/dl). The mixture was then shaken at room temperature for two hours during which time free hemoglobin was absorbed on the absorbent. The plasma separated from the absorbent contained 110.2 mg/dl free hemoglobin, resulting in a free hemoglobin extraction of 52.7%. Total protein concentration in the blood after the extraction was 5.5 g/dl. It was thus determined that the absorbent of the present invention absorbs free hemoglobin efficiently and selectively.

EXAMPLE 2

An absorbent was prepared following the same procedure as set forth in Example 1, except that L-tyrosine was used in place of tyramine as the phenol-containing compound. A hemoglobin absorption test was performed in the same manner as Example 1. The absorption and extraction rate for free hemoglobin was 42.0%.

EXAMPLE 3

An absorbent was prepared following the same procedure as set forth in Example 1, except that L-phenylalanine was used in place of tyramine as a phenyl-containing compound. A hemoglobin absorption test was performed in the same manner as Example 1. The absorption and extraction rate for free hemoglobin was 37.9%.

COMPARATIVE EXAMPLE 1

An absorbant was obtained by autoclave treatment of porous glass as in Example 1, except that the reaction was terminated before affixing the phenyl and/or phenol containing composition. The porous glass thus did not contain tyramine bound to the surface of the carrier with γ-glycydoxypropyltrimethoxysilane. An absorption test was performed as in Example 1. The absorption rate for free hemoglobin was 5.1%.

A comparison of the Examples 1,2,3 and Comparative Example 1 illustrates that the absorbents of this invention have excellent absorbability for free hemoglobin.

EXAMPLE 4

An absorbent was prepared following the same procedure as set forth in Example 1, except that FPG-100 (average pore size of 97A, specific surface area of 235 $m^2$/gm) was used as the porous glass carrier. An absorption test was performed in the same manner as Example 1. The absorption rate for free hemoglobin was 1.0%.

EXAMPLE 5

5 grams of silica gel MB-50, available from Fugi Davison Chemical (average pore size-100 A, specific surface area of 280 $M^2$/gm) was dipped into 100 ml of a 1.0% aqueous solution of γ-glycydoxyproyltrimethoxysilane. The preparation was then mixed for two hours to cause the silanol groups on the surface of the silica gel to react with the γ-glycydoxypropyltrimethoxysilane. After the two hours, the silica gel beads were filtered off and the water was wiped from their surface. The silica gel was then dried for three hours at a temperature of 120° C.

A 1% carbonate buffer solution was prepared for each of tyramine, L-tyrosine, L-phenylalanine and p-aminophenol. 1 gm of the prepared silica gel was then dipped separately into 50 ml each of the phenol or phenyl containing buffer solutions and the preparations were shaken at a temperature of 60° C. for 20 hours.

After the reaction was completed, the silica gels were washed with 0.1N sodium hydroxide solution and water to remove the non-reacted phenol or phenyl-containing compositions. The silica gels were then treated for two hours in an autoclave at 120° C. in order to open the chain of non-reacted epoxy groups. After treatment in the autoclave, the silica gels were washed with water. Four different absorbents were thus prepared, each comprising a silica gel porous carrier with a phenyl or phenol containing compound affixed to the surface of the carrier.

Hemoglobin absorption tests were performed on each of the four thus prepared absorbents. The results of the tests are set forth in Table 1 below.

TABLE 1

| Fixed Compound | Hemoglobin Absorption Rate |
|---|---|
| Tyramine | 70.7% |
| Tyrosine | 62.8% |
| Phenylalanine | 58.5% |
| p-aminophenol | 67.1% |

COMPARATIVE EXAMPLE 2

An absorbent was obtained by autoclave treatment of the silica gel as in Example 5, except that the reaction was terminated before affixing the tyramine. The silica gel thus did not contain tyramine bound to the surface thereof with γ-glycydoxypropyltrimethoxysilane. An absorption test was performed as in Example 1. The absorption rate for free hemoglobin was 32.90%.

EXAMPLE 6

An absorbent composed of silica gel MB-5D with its surface being fixed with tyramine was prepared following the same procedure as set forth in Example 5. This absorbent was filled into a column having an inner diameter of 4.4 mm and a length of 165 mm, thus making the inner volume 2.5 ml. Hemolyzed plasma was then passed into the column at a flow rate of 0.18 ml/min. The concentration of hemoglobin and total protein concentration of plasma which flowed out of the column at 10 minute intervals was determined. The absorption rate for free hemoglobin and total protein where calculated from the following formula:

$$\frac{[\text{Initial concentra.}] - [\text{After column concentra.}]}{[\text{Initial concentra.}]} \times 100 \, (\%)$$

The results of these determination are shown in Table 2.

TABLE 2

| | Absorption Rate (%) | |
|---|---|---|
| | Hemoglobin | Protein |
| 10 min. after | 96.1 | — |
| 20 | 86.4 | 21.4 |
| 30 | 83.9 | 15.7 |
| 40 | 78.7 | 11.4 |
| 50 | 67.1 | 10.0 |
| 60 | 61.3 | 7.1 |

EXAMPLE 7

Silica gel MB-5D was dipped into a 0.5% methanol aqueous solution (methanol concentration: 30%) of γ-glycydoxypropylmethyldiethoxysilane(Shin-etsu Kagaku-Kogyo's KBE402). The bubbles attached to the silica gel were removed by vacuum. The preparation was then mixed for one hour to cause the silanol groups on the surface of the silica gel to react with the γ-glycydoxy propylmethyldiethoxylsilane. Thereafter, the silica gel was removed from the silane solution, and the water was wiped from the surface of the silica gel. The thus prepared gel was then dried in a vacuum over night.

Subsequently, the silica gel was treated at a temperature of 160° C. for 2 hours, then dipped into a 1% aqueous tyramine solution at a temperature of 60° C. for 3 hours while shaking. The preparation was then left at room temperature for an over night so that the tyramine reacted with the epoxy groups of the silane compound. Thereafter, the silica gel was washed with water and treated in the autoclave at a temperature of 120° C. for 2 hours. After two hours, the preparation was washed with 2N hydrochloric acid solution followed by washing with water. The thus prepared absorbent was placed in a Soxhlet's Extractor and washed with water for a prescribed time length to extract the undesirable constituent. An absorbent was obtained with tyramine bound to its surface.

For the purpose of determining the eluate, 5 grams of the prepared absorbent were dipped into 50 ml of water. The preparation was then placed in the autoclave for 30 minutes. After 30 minutes, the absorbent was filtered, and 20 ml of the filtrate was evaporated to dryness, and the weight of precipitated solid was determined. The results are shown in the Table 3. The weights of eluate shown in the Table 3 are the converted value per 1 gram of absorbent.

TABLE 3

| Extraction time by Soxhlet's Extractor | Weight of Eluate |
|---|---|
| 3 hours | 1150 μg/gm |
| 6 hours | 860 |
| 9 hours | 690 |
| 16 hours | 480 |
| 19 hours | 420 |

For the purpose of testing the absorbability of the thus obtained absorbent, the absorbent was filled into a column and plasma containing 230 mg/dl of free hemoglobin was passed through for 70 minutes. The concentration of hemoglobin in plasma which outflowed from the column was measured. As a result, 75% of the free hemoglobin in the treated plasma had been absorbed, proving excellent absorbability for free hemoglobin.

EXAMPLE 8

An absorbent was prepared following the same procedure as set forth in Example 7, except that a 0.5% aqueous solution of γ-glycydoxypropyltrimethoxysilane (Shin-etsu Kagaku-Kogyo's KBM403), was used in place of the γ-glycydoxypropylmethyldiethoxysilane and the weights of the eluate were then determined. The results are shown in Table 4 below.

TABLE 4

| Extraction time by Soxhlet's Extractor | Weight of Eluate |
|---|---|
| 10 hours | 3940 g/gm |
| 18 hours | 2850 |
| 49 hours | 3780 |

As results in Table 4 illustrate, when silane compounds having three alkoxy groups bound to the silica element are used as the coupling agent, the volume of eluate may not drop even after washing. Accordingly, from a safety standpoint, it is preferred to use dialkoxysilanes having two alkoxy groups bound with its silica element. A hemoglobin absorption test performed on the washed absorbent shows an absorption rate of 73%.

EXAMPLE 9

An absorbent was prepared following the procedure set forth in Example 7, except that 10% acetic acid solution was used for washing in the Soxhlet's Extractor instead of washing with hydrochloric acid. The weight of the eluate was determined, the results of which are shown in the Table 5 below.

TABLE 5

| Extraction time by Soxhlet's Extractor | Weight of Eluate |
|---|---|
| 6 hours | 390 μg/g |
| 9 hours | 430 |
| 16 hours | 340 |

A comparison of the results summarized in Table 5 with the results summarized shown in Table 3, demonstrates that the use of acetic acid facilitates extraction of the eluate more readily than the use of hydrochloric acid. The hemoglobin absorption rate for the thus prepared absorbent was 71%.

EXAMPLE 10

In this example, 1.1 grams of free hemoglobin were injected into a mongrel adult dog weighting 11 kg. Extracorporeal circulation was performed, making use of the dog's femoral artery and vein. As shown schematically in FIG. 1, extracted blood was introduced into a plasma separator (a membrane type of plasma separator made by Nipro) through the femoral artery by a pump (3) at an extraction flow rate of 100 ml/min. The plasma and blood cells were separated from each other in the plasma separator, after which the separated plasma was supplied to an absorption column (2) (filled with 90 ml volume of absorbent which was prepared in a same manner as Example 9) by a pump (4) at a flow rate of 10 ml/min. The plasma was then remixed with perviously separated blood cells and returned to the dog's body through the femoral vein. The concentration of free hemoglobin before and after the column, as well as the free hemoglobin concentration in the dog's arterial blood were determined. The results are shown in the Table 6 below.

TABLE 6

| Time(min) | Free Hemoglobin Concentration (mg/ml) | | |
|---|---|---|---|
| | Column/inlet | Column/outlet | Arterial blood |
| 0 | — | — | 139 |
| 15 | 120 | 13 | 109 |
| 30 | 107 | 19 | 96 |
| 45 | 85 | 30 | 83 |
| 60 | 74 | 34 | 71 |
| 90 | 61 | 35 | 61 |
| 120 | 55 | 38 | 55 |
| 180 | 46 | 43 | 50 |

From this Example, it can again be seen that the use of an abosrbent of the present invention provides an efficient and selective absorption and extraction for free hemoglobin from blood. This absorbent may be easily produced, and may also be readily sterilized by autoclave and/or gamma rays, and is therefore excellent in practicality.

What is claimed is:

1. A method for extracting elevated amounts of free hemoglobin in blood comprising the steps of obtaining a sample of blood from a patient, said sample containing an elevated amount of free hemoglobin and contacting said blood with an absorbent comprising a carrier having phenyl and/or phenol groups on the surface of said carrier.

2. A method according to claim 1, wherein said carrier is a water insoluble porous carrier and said phenyl and/or phenol groups are provided as a composition comprising phenyl and/or phenol groups affixed to the surface of said carrier.

3. A method according to claim 2, wherein said porous carrier is selected from the group consisting of porous glass, porous silica, porous alumina, cellulose gel, agarose gel, dextran gel, polyacrylamide gel, vinyl polymer gel, and combinations thereof.

4. A method according to claim 2, wherein said porous carrier is selected from the group consisting of porous glass and porous silica.

5. A method according to claim 4, wherein said composition comprising phenyl and/or phenol groups is affixed to the surface of said carrier with a silane coupling agent.

6. A method according to claim 2, wherein said composition comprising phenyl and/or phenol groups is composed of more than one composition selected from the group consisting of tyramine, tyrosine, phenylalanine and aminophenol.

* * * * *